United States Patent
Allan et al.

(10) Patent No.: US 9,932,532 B2
(45) Date of Patent: *Apr. 3, 2018

(54) PRODUCTION OF BIODIESEL FROM OILS AND FATS VIA SUPERCRITICAL WATER

(71) Applicants: Graham Allan, Kenmore, WA (US);
Thomas E. Loop, Seattle, WA (US);
James D. Flynn, Auburn, WA (US)

(72) Inventors: Graham Allan, Kenmore, WA (US);
Thomas E. Loop, Seattle, WA (US);
James D. Flynn, Auburn, WA (US)

(73) Assignee: Xtrudx Technologies, Inc., Seattle, WA (US)

( * ) Notice: Subject to any disclaimer, the term of this patent is extended or adjusted under 35 U.S.C. 154(b) by 414 days.

This patent is subject to a terminal disclaimer.

(21) Appl. No.: 14/549,492

(22) Filed: Nov. 20, 2014

(65) Prior Publication Data

US 2015/0144837 A1 May 28, 2015

Related U.S. Application Data

(63) Continuation-in-part of application No. 13/297,217, filed on Nov. 15, 2011, now Pat. No. 8,980,143,
(Continued)

(51) Int. Cl.
*B29B 17/02* (2006.01)
*B29C 47/10* (2006.01)
(Continued)

(52) U.S. Cl.
CPC ............ *C10L 1/026* (2013.01); *B01J 3/008* (2013.01); *B01J 8/0045* (2013.01); *B01J 8/1836* (2013.01);
(Continued)

(58) Field of Classification Search
CPC . B29B 2017/0293; B29B 17/00; B29B 17/02; B29B 2017/00; B29B 2017/001;
(Continued)

(56) References Cited

U.S. PATENT DOCUMENTS 3,293,200 A * 12/1966 MacGregor ............ C09J 161/06
428/529
4,233,465 A * 11/1980 Gallivan ................... C08G 8/28
568/727

(Continued)

*Primary Examiner* — Joseph Drodge
(74) *Attorney, Agent, or Firm* — Thomas E. Loop

(57) ABSTRACT

A method for transforming selected renewable oils and fats, and optionally polyester waste plastic materials, into a plurality of reaction products via supercritical water is disclosed. The method comprises: conveying the selected oils and fats material through an extruder, wherein the extruder is configured to continuously convey the selected oils and fats material to a supercritical fluid reaction zone; injecting hot compressed water into the supercritical fluid reaction zone, while the extruder is conveying the selected oil and fats material into the supercritical fluid reaction zone so as to yield a mixture; retaining the mixture within the reaction zone for a period of time sufficient to yield the plurality of reaction products. The reaction zone may be characterized by a tubular reactor having an adjustably positionable inner tubular spear, wherein the tubular reactor and the inner tubular spear further define an annular space within the reaction zone, and wherein the mixture flows through the annular space and into a reaction products chamber.

8 Claims, 2 Drawing Sheets

Related U.S. Application Data which is a continuation-in-part of application No. 12/828,102, filed on Jun. 30, 2010, now Pat. No. 8,057,666, which is a continuation-in-part of application No. 12/402,489, filed on Mar. 11, 2009, now Pat. No. 7,955,508.

(60) Provisional application No. 61/035,380, filed on Mar. 11, 2008, provisional application No. 61/110,505, filed on Oct. 31, 2008, provisional application No. 61/906,655, filed on Nov. 20, 2013.

(51) Int. Cl.

| | | |
|---|---|---|
| *B29C 47/88* | (2006.01) | |
| *B01J 19/18* | (2006.01) | |
| *B01J 8/20* | (2006.01) | |
| *C07C 37/70* | (2006.01) | |
| *B01J 8/42* | (2006.01) | |
| *C08J 11/14* | (2006.01) | |
| *C07C 37/86* | (2006.01) | |
| *C10L 1/02* | (2006.01) | |
| *C07C 37/00* | (2006.01) | |
| *B01J 8/18* | (2006.01) | |
| *B01J 19/08* | (2006.01) | |
| *B01J 3/00* | (2006.01) | |
| *B01J 8/00* | (2006.01) | |

(52) U.S. Cl.
CPC . *B01J 8/20* (2013.01); *B01J 8/42* (2013.01); *B01J 19/087* (2013.01); *B29B 17/02* (2013.01); *B29C 47/10* (2013.01); *C07C 37/004* (2013.01); *C07C 37/005* (2013.01); *C07C 37/70* (2013.01); *C08J 11/14* (2013.01); *B01J 2219/089* (2013.01); *B01J 2219/0854* (2013.01); *B01J 2219/182* (2013.01); *C10L 2200/0476* (2013.01); *C10L 2270/026* (2013.01); *C10L 2290/146* (2013.01); *Y02E 50/13* (2013.01); *Y02P 20/544* (2015.11)

(58) Field of Classification Search
CPC ..... B29C 47/00; B29C 47/10; B29C 47/1009; B29C 47/1018; B29C 47/109; B29C 47/40; B29C 47/88; B29C 47/8805; C07C 37/00; C07C 37/005; C07C 37/68; C07C 37/685; C07C 37/70; C07C 37/72; C07C 37/86; C07C 37/004; C07C 37/006; C08J 11/00; C08J 11/14; C08J 11/16; C08J 11/10; B01J 19/087; B01J 19/18; B01J 19/1812; B01J 19/1843; B01J 19/24; B01J 19/244; B01J 19/2415; B01J 2219/00891; B01J 2219/00896; B01J 2219/0869; B01J 2219/19; B01J 2219/1943; B01J 2219/24; B01J 2219/2418; B01J 2219/2419; B01J 2219/2422; B01J 2219/2425; B01J 2219/2441; B01J 2219/2448; B01J 8/20; B01J 8/42; B01J 3/008; B01J 8/1836; B01J 8/0045; B01J 2219/089; B01J 2219/182; B01J 2219/0854; B01J 8/008; B01J 16/00; B01J 8/00; B01J 2017/0203; Y02P 20/544; B01D 17/00; B01D 17/005

USPC ........ 210/175, 177, 180–182, 259, 511, 634, 210/639, 758–761, 774, 749, 808; 264/37.1, 37.18, 211.21, 211.23, 211.24, 264/11–13, 454; 241/20, 24, 28; 44/307, 44/308, 605, 606; 422/138, 198, 199, 422/208, 602, 606, 608, 618, 242, 211, 422/224; 219/600, 618, 628, 630, 635; 71/11–13; 554/8–23, 174, 175; 528/480, 528/483, 502, 502 R, 502 A, 502 F, 503

See application file for complete search history.

(56) References Cited

U.S. PATENT DOCUMENTS

| | | | | |
|---|---|---|---|---|
| 4,942,269 | A * | 7/1990 | Chum | C07C 37/005 208/96 |
| 5,223,601 | A * | 6/1993 | Chum | C07C 37/52 428/514 |
| 5,386,055 | A * | 1/1995 | Lee | B01J 3/008 210/180 |
| 5,807,952 | A * | 9/1998 | Agblevor | C07B 41/02 527/400 |
| 6,660,236 | B1 * | 12/2003 | Kodama | C08J 11/14 422/187 |
| 6,676,716 | B2 * | 1/2004 | Fujimura | C10J 3/523 422/140 |
| 7,235,219 | B2 * | 6/2007 | Nakajima | C08J 3/09 264/211.21 |
| 7,399,408 | B2 * | 7/2008 | Joussot-Dubien | A62D 3/20 210/179 |
| 7,799,835 | B2 * | 9/2010 | Smith | B29B 17/02 209/552 |
| 7,923,039 | B2 * | 4/2011 | Cornish | B01D 11/0284 209/12.1 |
| 7,955,508 | B2 * | 6/2011 | Allan | B01J 3/008 210/749 |
| 8,057,666 | B2 * | 11/2011 | Allan | B01J 3/008 210/175 |
| 8,342,735 | B2 * | 1/2013 | Black | C12M 35/04 366/78 |
| 8,980,143 | B2 * | 3/2015 | Loop | B01J 3/008 210/175 |
| 2003/0021915 | A1 * | 1/2003 | Rohatgi | B27N 3/007 428/15 |
| 2003/0042645 | A1 * | 3/2003 | Ichikawa | B29C 47/0007 264/102 |
| 2005/0242464 | A1 * | 11/2005 | Goto | B29B 17/02 264/211.24 |
| 2007/0148320 | A1 * | 6/2007 | Uchiyama | B29C 47/585 426/634 |
| 2007/0161095 | A1 * | 7/2007 | Gurin | C12P 7/10 435/134 |
| 2008/0113146 | A1 * | 5/2008 | Wright | B29B 17/02 428/95 |
| 2009/0056201 | A1 * | 3/2009 | Morgan | C11B 13/005 44/308 |
| 2009/0234093 | A1 * | 9/2009 | Schulz Van Endert | B01F 7/00458 528/271 |
| 2010/0210745 | A1 * | 8/2010 | McDaniel | C09D 5/008 521/55 |

* cited by examiner

PRODUCTION OF BIODIESEL FROM OILS AND FATS VIA SUPERCRITICAL WATER

CROSS-REFERENCE TO RELATED APPLICATIONS

This application is a continuation-in-part of U.S. application Ser. No. 13/297,217 filed on Nov. 15, 2011 (allowed), which application claims the benefit of priority to U.S. application Ser. No. 12/828,102 filed on Jun. 30, 2010 (now U.S. Pat. No. 8,057,666) and U.S. application Ser. No. 12/402,489 filed on Mar. 11, 2009 (now U.S. Pat. No. 7,955,508), which applications claims the benefit of priority to U.S. Provisional Application No. 61/035,380 filed on Mar. 11, 2008 and U.S. Provisional Application No. 61/110,505 filed on Oct. 31, 2008, which applications are all incorporated herein by reference in their entireties for all purposes. This application also claims the benefit of priority to U.S. Provisional Application No. 61/906,655 filed on Nov. 20, 2013.

TECHNICAL FIELD

The present invention relates generally to biomass and waste plastic conversion systems and, more specifically, to machines and methods of transforming naturally-occurring, renewable oils and fats into smaller molecules by reaction with a hot compressed and/or supercritical water.

BACKGROUND OF THE INVENTION

Everyday the Sun pours down onto the Earth a vast quantity of radiant energy many many times greater than the total now used by Man. Some of this energy, together with carbon dioxide and water, Nature traps in trees and other plants by conversion into oils and fats. As they exist in the plants these materials are unsuitable for use as diesel engine fuels. However. the energy trapped within the oils and fats of the plants can be recovered, in part, by breaking down the complex chemical structures of the oils and fats into a mixture of the water-soluble trifunctional alcohol, glycerol, and various fatty carboxylic acids. Thereafter by conventional procedures the fatty acids can be esterified with methanol to yield biodiesel. The breakdown reaction of oils and fats is usually conventionally accomplished in batch reactors by protracted heating of the oils and fats with water to which a basic catalyst, such as sodium hydroxide or potassium hydroxide, has been added. The time of the breakdown reaction is several hours because batch reactors are intrinsically inefficient in comparison to continuous reactors. This batch reaction time can be somewhat reduced by replacement of the hydroxide catalyst with sodium methylate or potassium methylate. These catalysts are difficult to ship because of their ready reaction with moisture. Storage is also a problem for the same reason. Manufacture of the catalysts at the actual location of the oils and fats breakdown process by the reaction of elemental sodium or potassium metals with methanol is troublesome and hazardous. Moreover, the use of either of these catalysts leads to the formation of the sodium or potassium salts of the fatty acids generated by the breakdown of the oils and fats. Such salts are known as soaps and can cause costly chemical engineering difficulties such as foaming as well as emulsion formation. Finally, the water-soluble sodium or potassium salts of the fatty acids must be destroyed by treatment with mineral acids to liberate the free water-insoluble fatty acids for subsequent reaction with methanol to form the so-called biodiesel. This acid treatment step produces the sodium or potassium salts of the mineral acid as a waste product which must be disposed of subsequently. The problem facing chemical engineers has been how to achieve these several sequential chemical reactions on a large-scale, commercially practical, and energy efficient way.

Nowadays, everyone is aware of the desirability of having new domestic sources of liquid fuels for diesel engines and as a result inefficient conventional processes for the conversion of oils and fats to biodiesel have been developed.

One of the most intriguing and environmentally sound approaches to breaking down molecules is simply to use water alone, heated to its supercritical state. About a decade ago this chemical-free technology was comprehensively discussed in an English language review by P. E. Savage (Chem. Rev. 1999, 99, 609). Since then few modern reviews have appeared. However, numerous articles, mostly from Japan and China, have appeared each year dealing with the reactive power of supercritical water. All of these publications emphasize that when water is heated to 374.4 C or above, the pressure concomitantly generated is 217.7 atm and above. The water then becomes a powerful new reactive solvent. Temperatures above 400 C seem to make the water even more effective in its new role. For example, it now dissolves nonpolar substances such as oils and fats.

These and numerous other similar reactions (J. A. Onwudili & P. T. Williams, Chemosphere 2009, 74(6), 787) demonstrate clearly that chemical bonds can be broken down by treatment with supercritical water only, without the use of any catalysts. Apparently the water and substrates may undergo the water gas reaction and hydrogen is released to combine with the molecular fragments from the substrates. This has actually been demonstrated by the use of deuterium oxide in place of water and the consequent finding of deuterium in the fragments. However, since nearly all water-substrate reactions have been run in a batch mode on a very small scale, the chemistry so elegantly elucidated does not provide answers to the questions necessary for the future development of a commercially-sized, practical, continuous, supercritical water-based process.

As is commonly understand by those with backgrounds in chemical engineering, petroleum-based diesel fuels are produced from the fractional distillation of crude oil between 200 C (392° F.) and 350° C. (662° F.) at atmospheric pressure, resulting in a mixture of carbon chains that typically contain between 8 and 21 carbon atoms per molecule. Diesel fuels are approximately similar to fuel oils used for heating (fuel oils no. 1, no. 2, and no. 4). All fuel oils consist of complex mixtures of aliphatic and aromatic hydrocarbons. The aliphatic alkanes (paraffins) and cycloalkanes (naphthenes) are hydrogen saturated and compose approximately 80-90% of the fuel oils. Aromatics (e.g., benzene) and olefins (e.g., styrene and indene) compose 10-20% and 1%, respectively, of the fuel oils. Fuel oil no. 1 (straight-run kerosene) is a light distillate which consists primarily of hydrocarbons in the C9-C16 range; fuel oil no. 2 is a heavier, usually blended, distillate with hydrocarbons in the C11-C20 range. Straight-run distillates may also be used to produce fuel oil no. 1 and diesel fuel oil no. 1. Diesel fuel no. 1 and no. 2 are similar in chemical composition to fuel oil no. 1 and fuel oil no. 2, respectively, with the exception of the additives. Diesel fuels predominantly contain a mixture of C10 through C19 hydrocarbons, which include approximately 64% aliphatic hydrocarbons, 1-2% olefinic hydrocarbons, and 35% aromatic hydrocarbons.

Accordingly, and although some progress has made with respect to the development of renewable systems for the manufacture of non-petroleum diesel fuel, there is still a need in the art for new and improved machines, systems, and methods for the continuous conversion of plant or animal material into liquid transportation fuels. The present invention fulfills these needs and provides for further related advantages.

SUMMARY OF THE INVENTION

The present invention in one embodiment is directed to a new method for transforming a selected renewable material into a plurality of reaction products. The innovative method of the present invention comprises at least the following steps: conveying the selected renewable material (e.g., a plant- or animal derived oil or fat or a combination thereof) through an extruder (single or twin screw) so as to define a selected oil or fat material flowstream, wherein the extruder is configured to continuously convey the selected material from an upstream inlet to a supercritical fluid reaction zone; injecting hot compressed water into the supercritical fluid reaction zone while the extruder is conveying the selected oil or fat material flowstream into the supercritical fluid reaction zone so as to yield a mixture; retaining the mixture within the reaction zone for a period of time (e.g., from about 0.4 to about 10 seconds) sufficient to yield the plurality of reaction products, wherein the reaction zone is defined by a tubular reactor shell having an inner tubular spear, wherein the tubular reactor and the inner tubular spear further define an annular space within the reaction zone, and wherein the mixture flows through the annular space (and wherein the inner tubular spear is adjustably movable in back and forth directions within the tubular reactor so as to selectably increase or decrease the volume of the reaction zone); and expelling the plurality of reaction products out of the supercritical fluid reaction zone and into a reaction products chamber. The method may further comprise a step of easily separating the plurality of reaction products into an aqueous phase and a non-aqueous phase without the use of mineral acids and the concomitant generation of waste salts.

In another embodiment, the present invention is directed to an innovative tube and spear reactor as herein shown and described, as well as to related extruder-based machinery and fluid expansion chambers.

These and other aspects of the present invention will become more evident upon reference to the following detailed description and accompanying drawings. It is to be understood, however, that various changes, alterations, and substitutions may be made to the specific embodiments disclosed herein without departing from their essential spirit and scope.

BRIEF DESCRIPTION OF THE DRAWINGS

The drawings are intended to be illustrative and symbolic representations of certain exemplary embodiments of the present invention and as such they are not necessarily drawn to scale. In addition, it is to be expressly understood that the relative dimensions and distances depicted in the drawings are exemplary and may be varied in numerous ways. Finally, like reference numerals have been used to designate like features throughout the views of the drawings.

DETAILED DESCRIPTION OF INVENTION

Figure 1:
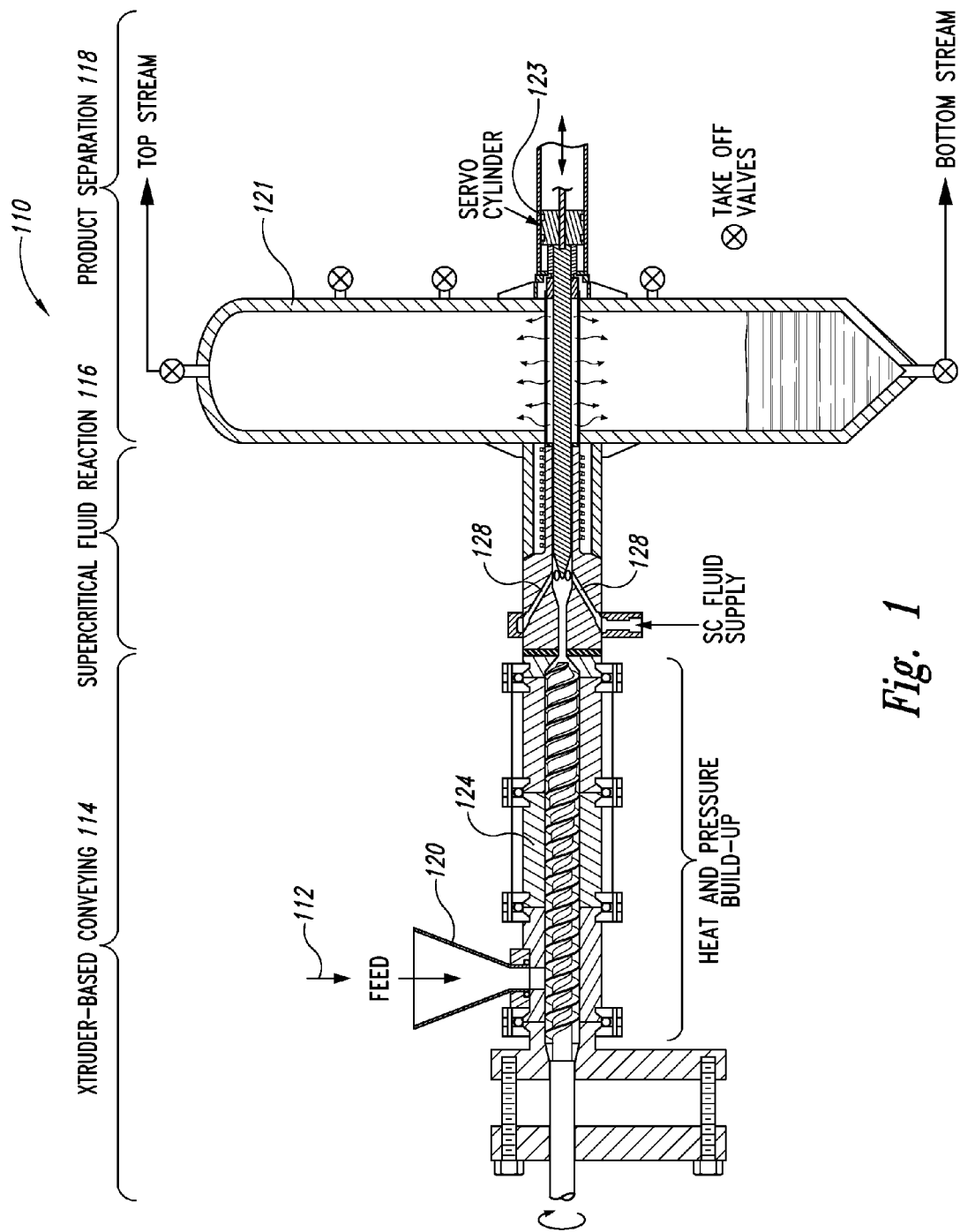
FIG. 1 shows a side elevational cross-sectional view of an extruder-fed induction-heated supercritical fluid conversion machine in accordance with an embodiment of the present invention.
Figure 2:
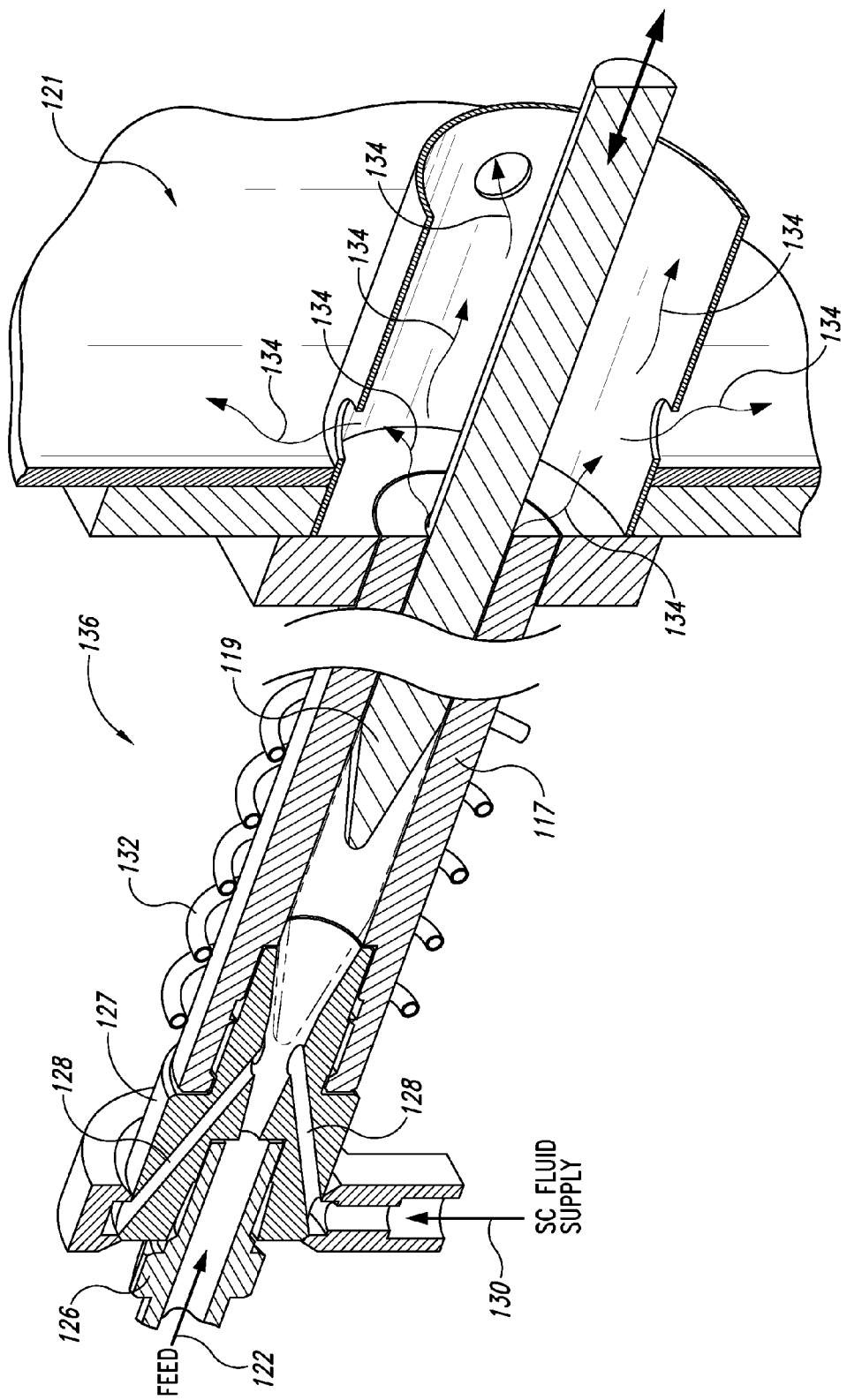
FIG. 2 shows a partial cross-sectional view of a supercritical fluid reaction zone defined by a spear-and-tube reactor in accordance with an embodiment of the present invention.

Referring now to the drawings where like numerals have been used to designate like features throughout the views, and more specifically to FIGS. 1 and 2, the present invention in one embodiment is directed to a supercritical fluid conversion machine/system 110 capable of converting a selected oil or fat material 112 into a plurality of reaction products (not shown). In the context of the present invention, the term "oil or fat" means any plant- or animal-derived organic matter, containing numerous linkages of fatty acids to alcohols.

As shown, the oil and fat conversion machine/system 110 of the present invention comprises, in fluidic series, three discreet zones: namely, (1) an extruder-based conveying zone 114; (2) a supercritical fluid reaction zone 116; and (3) a reaction products separation zone 118.

In accordance with the novel approach of the present invention, a specialized extruder conveys the selected oil or fat materials 112 from an upstream hopper 120 to the downstream supercritical fluid reaction zone 116, while increasing the pressure from about atmospheric to greater than about 3,200 psi. The extruder-based approach is important because it enables the conveyance of near-solid materials (as opposed to conventional slurry pumping technologies used in the prior art). The heated and pressurized oil and fat materials 122 exit the extruder 124 through a specialized die 126 connected to a manifold 127 that includes a plurality of circumferentially positioned supercritical fluid injection channels 128 configured to inject hot compressed water 130 (or other fluid) into the supercritical fluid reaction zone 116.

In a preferred embodiment, hot compressed water 130 is injected into the supercritical fluid reaction zone 116 by way of the injection channels 128 while the extruder 124 is conveying the selected polymeric materials 112 into the supercritical fluid reaction zone 116 so as to yield a mixture (not shown). The supercritical fluid reaction zone 116 further heats the flowing and pressurized polymeric materials 122 and hot compressed water 130 mixture to conditions at or above supercritical by means of a circumferentially positioned, high efficiency alternating current induction coil 132 (which, in turn, is connected to an induction heater (not shown)) to thereby yield the plurality of reaction products 134. The resulting liquefied and/or gaseous reaction products 134 are then conveyed through a highly innovative spear-and-tube reactor 136.

As best shown in FIG. 2, the spear-and-tube reactor 136 of the present invention allows a controlled and/or minimal amount of supercritical water to enter into the system (i.e., preferably less than about 100% to about 20% by weight basis). More specifically, the reaction zone 116 is defined by a tubular reactor shell 117 having an inner tubular spear 119, wherein the tubular reactor shell 117 and the inner tubular spear 119 further define an annular space within the reaction zone. As shown, the oil or fat materials 122 and hot compressed water 130 mixture yield the plurality of reactions products 134 that flow through the annular space and are expelled into an innovative expansion/separation chamber 121. The expansion/separation chamber 121 preferably contains liquid water and a hydrocarbon solvent to facilitate liquid-liquid extraction and phase separation of the resulting fatty acid mixture and glycerol-containing water. As further shown, the inner tubular spear 119 is adjustably movable in back and forth directions within the tubular reactor shell 117 by means of a servo cylinder 123 so as to selectable increase or decrease the volume of the reaction zone.

Without necessarily prescribing to any particular scientific theory, it is believed that at supercritical conditions the water component is at a supercritical state, thereby enabling (in the context of a selected oil and/or fat) the rapid hydrolysis of the ester linkages therein. and simultaneously capture of hydrogen atoms and hydroxyl moieties from the water. As a consequence, a whole range of free fatty carboxylic acid of various lengths are formed. When these are reacted with methanol the resultant methyl esters have been found to be soluble in regular diesel and may be readily utilized in the automobile fuel market as a drop-in additive.

The present invention is also directed to a method for converting oils and fats into a plurality of reaction products. Accordingly, and in another embodiment, a method of the present invention comprises the steps of: providing an elongated conveying zone that contains two or more elongated rotatable shafts having a plurality of flighted screws positioned lengthwise within an elongated conveying section housing, wherein the plurality of flighted screws are positioned about each respective two or more elongated rotatable shafts, and wherein the two or more elongated rotatable shafts are configured to continuously convey the selected oils and fats (optionally together with water or other liquid) from an upstream inlet to a supercritical fluid reaction zone while increasing the pressure of the selected oils and fats biomass from about atmospheric at the inlet to greater than about 22.1 MPa at the supercritical fluid reaction zone; conveying a mixture of the selected oils and fats biomass material through the elongated conveying zone and into the supercritical fluid reaction zone; heating and further pressurizing the mixture within the supercritical fluid reaction zone, while injecting hot compressed and/or supercritical water into the supercritical fluid reaction zone, to yield a plurality of reaction products, wherein heat energy is supplied by means of an induction heating coil positioned circumferentially about the supercritical fluid reaction zone; retaining the mixture within the supercritical fluid reaction zone for a period of time sufficient to yield the plurality of reaction products; expelling the plurality of reaction products out of the supercritical fluid reaction zone and into a separation zone; and separating the plurality of reaction products into at least a water-soluble fraction and an organic solvent soluble fraction.

In this method, the period of time that the oil and fat mixture is retained within the supercritical fluid reaction zone generally ranges from about 0.4 to about 10 seconds (but may include much greater periods of time up to a few minutes in duration). This method may also comprises the further steps of adding a plurality of electrically conductive particles to the mixture of the selected oils and fats and water such the plurality of electrically conductive particles are heated while passing through the induction coil.

Waste polyester plastics from beverage bottles and the like can also be included with the oils and fats so that the products of the continuous reaction with supercritical water will comprise water-insoluble terephthalic acid and water-soluble ethyleneglycol. In the subsequent esterification with methanol or other monofunctional alcohol the terephthalic acid will become a diester suitable as a diesel fuel component.

Finally, and for purposes of efficient heat transfer across the flowing oil and fat biomass stream (with or without the addition of waste polyester plastic) it is contemplated that a suitable heat transfer agent such as, for example, a recyclable low melting metal (tin, mp 232° C. or lead, mp 327° C.) or metal alloy, preferably Wood's metal (an alloy of Bismuth 50%, Cadmium 12.5%, Lead 25% and Tin 12.5%, mp 73-77° C.) may be added to the oil or fat biomass feedstock prior to its introduction into a single or co-rotating twin screw extruder.

While the present invention has been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

What is claimed is:

1. A method for transforming selected renewable material comprising oils, fats or a combination thereof material with or without the presence of waste polyester plastic, into a plurality of reaction products including diesel fuel formulations, the method comprising the steps of:
   conveying the selected oils and/or fats material through an extruder so as to define a selected material flowstream, wherein the extruder is configured to continuously convey the selected oils and /or fats material from an upstream inlet to a supercritical fluid reaction zone;
   injecting hot compressed water into the supercritical fluid reaction zone while the extruder is conveying the selected oils and fats material flowstream into the supercritical fluid reaction zone so as to contact the feedstock or admixture with supercritical water to yield a mixture;
   retaining the mixture within the reaction zone for a period of time sufficient to yield the plurality of reaction products including the diesel fuel formulations, wherein the reaction zone is defined by a tubular reactor having an inner tubular spear, wherein the tubular reactor and the inner tubular spear further define an annular space within the reaction zone, and wherein the mixture flows through the annular space; and
   expelling the plurality of reaction products out of the supercritical fluid reaction zone and into a reaction products chamber.

2. The method of claim 1 wherein the selected oils and/or fats are a renewable biomass.

3. The method of claim 2 wherein the extruder is a single screw extruder.

4. The method of claim 2 wherein the hot compressed water is supercritical water.

5. The method of claim 4 wherein the hot compressed water is in an amount that is less than the amount of the selected oils and/or fats on a weight percent basis.

6. The method of claim 2 wherein the period of time ranges from about 0.4 to about 10 seconds.

7. The method of claim 2 wherein the inner tubular spear is adjustably movable in back and forth directions within the tubular reactor so as to selectably increase or decrease the volume of the reaction zone.

8. The method of claim 7, further comprising the step of separating the plurality of reaction products into an aqueous phase and a non-aqueous phase.

* * * * *